United States Patent
Caspers

(10) Patent No.: US 10,668,227 B2
(45) Date of Patent: Jun. 2, 2020

(54) SKIN-ATTACHABLE DRUG INJECTION DEVICE WITH DETACHMENT SENSOR

(71) Applicant: Sanofi, Paris (FR)

(72) Inventor: Michael Caspers, Frankfurt am Main (DE)

(73) Assignee: Sanofi, Paris (FR)

( * ) Notice: Subject to any disclaimer, the term of this patent is extended or adjusted under 35 U.S.C. 154(b) by 624 days.

(21) Appl. No.: 15/504,751

(22) PCT Filed: Sep. 11, 2015

(86) PCT No.: PCT/EP2015/070872
§ 371 (c)(1),
(2) Date: Feb. 17, 2017

(87) PCT Pub. No.: WO2016/041873
PCT Pub. Date: Mar. 24, 2016

(65) Prior Publication Data
US 2017/0259015 A1 Sep. 14, 2017

(30) Foreign Application Priority Data

Sep. 15, 2014 (EP) .................................. 14306421

(51) Int. Cl.
*A61M 5/14* (2006.01)
*A61M 5/50* (2006.01)
(Continued)

(52) U.S. Cl.
CPC ...... *A61M 5/5086* (2013.01); *A61M 5/14248* (2013.01); *A61M 5/20* (2013.01);
(Continued)

(58) Field of Classification Search
CPC ............ A61M 5/5086; A61M 5/14248; A61M 2005/14268; A61M 2205/13;
(Continued)

(56) References Cited

U.S. PATENT DOCUMENTS 5,423,748 A * 6/1995 Uhala ............... A61M 5/16836
128/DIG. 13
2004/0116866 A1 * 6/2004 Gorman ............ A61M 5/14248
604/174

(Continued)

FOREIGN PATENT DOCUMENTS

CN 103717246 4/2014
WO WO 2006/067217 6/2006
(Continued)

OTHER PUBLICATIONS

International Search Report and Written Opinion in International Application No. PCT/EP2015/070872, dated Nov. 27, 2015, 16 pages.
(Continued)

*Primary Examiner* — Kevin C Sirmons
*Assistant Examiner* — Tezita Z Watts
(74) *Attorney, Agent, or Firm* — Fish & Richardson P.C.

(57) ABSTRACT

A medicament delivery device including at least one contact sensor configured to output a signal representing a state of partial detachment of the device from an injection site, and an alert output module configured to output an alert based on the signal received from the at least one contact sensor.

20 Claims, 4 Drawing Sheets

(51) Int. Cl.
*A61M 5/142* (2006.01)
*A61M 5/20* (2006.01)
*A61M 5/145* (2006.01)

(52) U.S. Cl.
CPC . *A61M 5/1452* (2013.01); *A61M 2005/14252* (2013.01); *A61M 2005/14268* (2013.01); *A61M 2205/13* (2013.01); *A61M 2205/14* (2013.01); *A61M 2205/18* (2013.01); *A61M 2205/3306* (2013.01); *A61M 2205/3317* (2013.01); *A61M 2205/3344* (2013.01); *A61M 2205/3368* (2013.01); *A61M 2205/3561* (2013.01); *A61M 2205/3569* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2205/8206* (2013.01)

(58) Field of Classification Search
CPC .......... A61M 2205/14; A61M 2205/18; A61M 2205/3317; A61M 2205/3368; A61M 2205/3569; A61M 2205/3584; A61M 2205/50; A61M 2205/52; A61M 2205/581; A61M 2205/582; A61M 2205/583; A61M 2205/8206; A61B 5/14532; A61B 5/02455
See application file for complete search history.

(56) References Cited

U.S. PATENT DOCUMENTS

| 2008/0281276 | A1  | 11/2008 | Shekalim |
| 2008/0281297 | A1* | 11/2008 | Pesach .............. A61M 5/14244 604/890.1 |
| 2009/0145446 | A1* | 6/2009  | DeDecker ............. A61M 25/01 128/899 |
| 2012/0078181 | A1  | 3/2012  | Smith et al. |
| 2014/0272861 | A1* | 9/2014  | Bergman ............... G09B 23/28 434/262 |

FOREIGN PATENT DOCUMENTS

| WO | WO 2006/120253 | 11/2006 |
| WO | WO 2010/029054 | 3/2010 |
| WO | WO 2011/133823 | 10/2011 |
| WO | WO 2012/032411 | 3/2012 |
| WO | WO 2012160159  | 11/2012 |

OTHER PUBLICATIONS

International Preliminary Report on Patentability in International Application No. PCT/EP2015/070872, dated Mar. 21, 2017, 10 pages.

* cited by examiner

SKIN-ATTACHABLE DRUG INJECTION DEVICE WITH DETACHMENT SENSOR

CROSS-REFERENCE TO RELATED APPLICATIONS

This application is a U.S. national stage application under 35 USC § 371 of International Application No. PCT/EP2015/070872, filed on Sep. 11, 2015, which claims priority to European Patent Application No. 14306421.0, filed on Sep. 15, 2014, the entire contents of each of which are hereby incorporated by reference.

FIELD

The present disclosure relates to a partial detachment sensor and, in particular, to a sensor for detecting partial detachment of a medicament delivery device from an injection site.

BACKGROUND

A variety of diseases exist that require regular treatment by injection of a medicament. Such injections can be performed by using injection devices, which are applied either by medical personnel or by patients themselves. As an example, type-1 and type-2 diabetes can be treated by patients themselves by injection of insulin doses, for example once or several times per day. Biological medicaments are being increasingly developed which comprise higher viscosity injectable liquids and which are to be administered in larger volumes than long-known liquid medicaments. Large volume devices ("LVDs") for administering such biological medicaments may comprise a pre-filled disposable drug delivery device or, alternatively, a disposable drug delivery device into which a patient or medical personnel must insert a drug cartridge prior to use.

Such LVDs are conventionally worn over relatively long periods, for example over one or more days. As patients go about their day-to-day business, there is a possibility that certain activities may lead to the attachment of the device to degrade over this time period. There is therefore a need to allow patients to maintain their routines and remain active while the injection is administered.

SUMMARY

According to a first aspect, there is provided a medicament delivery device comprising at least one contact sensor configured to output a signal representing a state of partial detachment of the device from an injection site, and an alert output configured to output an alert based on the signal received from the at least one contact sensor. The device outputs an alert after detection of partial detachment, i.e. before complete detachment of the device from an injection site.

The at least one contact sensor may be a plurality of contact sensors located at discrete locations on a contact surface of the device. This allows detachment information to be mapped around the surface of the contact region.

Some or all of the contact sensors may be disposed proximate the outer edge of the contact surface. This gives information from an area of the device likely to become detached first.

The detection of partial detachment may comprise detecting that a subset of the plurality of the sensors has become detached from the injection site.

The device may be configured to output one or more further alerts having progressively higher severity levels as the degree of detachment of the device from the injection site increases. This provides variable alert levels depending on the severity of device detachment.

The device may be configured to continue injecting the medicament at a reduced injection flow rate if a non-zero degree of partial detachment does not exceed an injection halt threshold. This reduces disruption to the injection.

The device may be configured to halt the injection in response to a determination that the degree of detachment of the device from the injection site exceeds an injection halt threshold. This provides a failsafe in case partial detachment alerts are not heeded by the patient.

The degree of detachment of the device may be determined by the number of sensors that have become detached from the injection site or by the magnitude of a signal output by the one or more sensors.

The alert may be automatically deactivated in response to a detection that the device has been re-attached to the injection site. This allows automated deactivation so that a separate deactivation step is not required.

The device may be configured to lower a detachment threshold at which a particular alert is output in comparison to the threshold at which the same alert was outputted during a previous detachment event.

The alert may be a notification sent through a wireless network to a mobile communications device.

The alert may be at least one of: an auditory alert; a visual alert; a vibrational feedback alert.

The one or more sensors may comprise a temperature sensor and/or a resistive sensor, and/or a capacitive sensor.

The device may be a bolus medicament delivery device.

The device may further comprise a controller, wherein the controller is configured to control the sensor and the alert output to output an alert based on the signal received from the at least one contact sensor.

The alert may be dependent on information relating to the severity of device detachment.

According to a second aspect, there is provided a system comprising the device and a reservoir of medicament to be delivered into a patient by injection.

According to a third aspect, there is provided a method of delivering a medicament using a medicament delivery device, the method comprising outputting, from at least one contact sensor, a signal representing a state of partial detachment of the device from an injection site, and, based on the signal received from at least one contact sensor, outputting an alert based on the signal received from the at least one contact sensor.

BRIEF DESCRIPTION OF THE DRAWINGS

For the purpose of example only, embodiments are described below with reference to the accompanying figures in which.

DETAILED DESCRIPTION

A wearable fluid delivery device for delivering fluid medicament to a patient is described below. The device comprises a reservoir for storing a quantity of medicament and a dispensing interface for delivering the medicament to the patient. The device is configured to deliver the medicament from the dispensing interface by injection and to sense partial or complete detachment of the device from the patient's skin.

For the sake of discretion, a patient will likely want to place the device 1 under clothing so that the device is not visible during use. The patient may not become aware that the device 1 has become partially detached since he or she cannot see the device. The patient may also not feel the device 1 becoming detached as they may have lost the sensation on the part of their body where the device is to be placed. For example, people suffering from diabetes are known to develop difficulties relating to their senses of sight and touch.

The detachment detection functionality notifies a patient if the device becomes partially detached from the patient's skin. By alerting the patient to partial detachment of the device, the patient can re-attach the device before it becomes completely detached, thereby avoiding an interruption in the delivery of the medicament.

Figure 1:
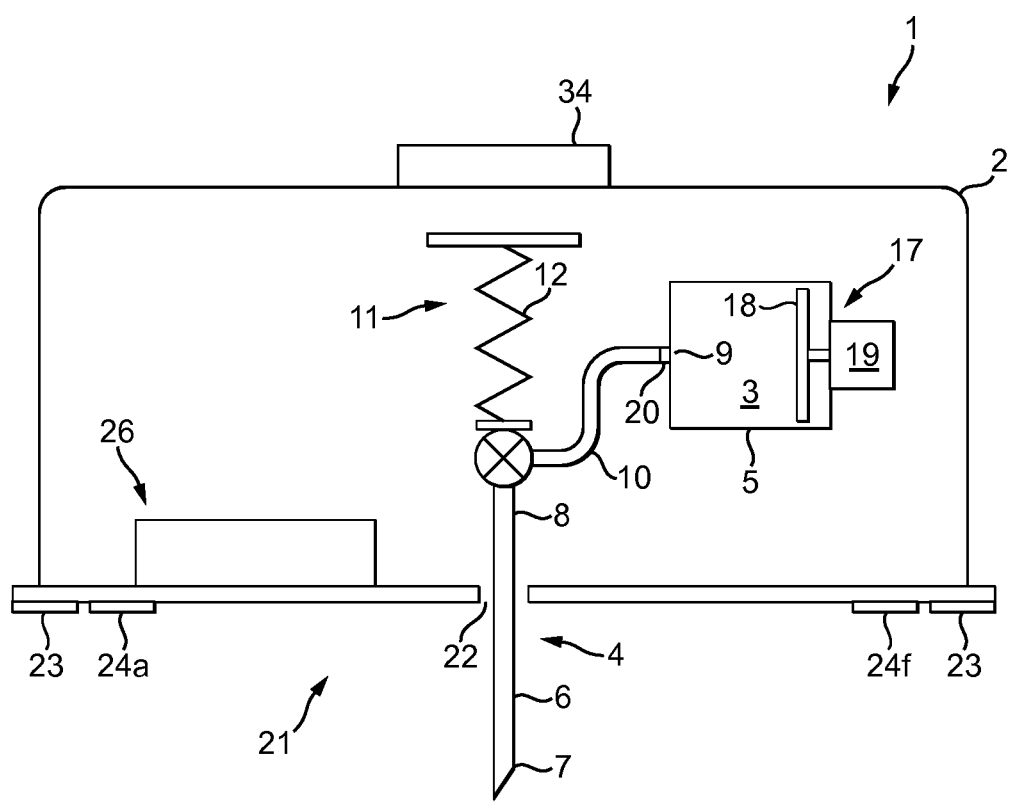
FIG. 1 is a schematic illustration of a wearable device.

Referring to the exemplary embodiment shown in FIG. 1, the device 1 comprises a protective housing 2 in which the reservoir of medicament 3 and the dispensing interface 4 are located together with other components of the device 1. The housing 2 is formed from moulded plastics or another suitable material. The reservoir of medicament 3 is provided in a capsule 5, which may contain a single dose of the medicament. The capsule 5 is formed of inert material such as glass and is secured inside an internal cavity of the housing 2. The capsule 5 may be replaceable to allow re-use of the device 1. Alternatively, the capsule 5 may be non-replaceable in the device 1 so that, once the contents of the capsule 5 has been exhausted, the device 1 can no longer be used to deliver medicament and must be disposed of. This single-use nature of the device 1 facilitates ease of operation and improves safety by ensuring that a patient cannot mistakenly install an incorrect replacement capsule.

The dispensing interface 4 comprises an injection element for injection of the medicament from the device 1 into the patient. The injection element is explained below in the context of a cannula 6, as illustrated in FIG. 1. The cannula 6 comprises a distal end 7, which during use protrudes through the housing 2 of the device 1 into the tissue of the patient. The cannula 6 also comprises a proximal end 8, which is arranged to receive medicament from the reservoir 3 referred to above. For example, an opening 9 in the form of an exit port in the capsule 5 may be connected to the proximal end 8 of the cannula 6 by a conduit 10 so that fluid medicament can flow from the capsule 5 into the cannula 6. As explained below, the cannula 6 can include a needle or other suitable injection element.

The cannula 6 may be controllably extendable and/or retractable through the exterior of the housing 2 in order to allow it to be safely stowed in the housing 2 when not in use. The device 1 may contain a user-operable actuator 11 to facilitate this. The actuator 11 is configured to cause movement of the cannula 6 relative to the housing 2 of the device 1 in order to extend and/or retract the cannula 6. An example is an actuator 11 that comprises a sprung element 12 and a switch 13 for releasing the sprung element 12. Upon release by the switch 13, the sprung element 12 may be configured to automatically extend and thereby drive the cannula 6 partially out of the housing 2 into an injection position. In other embodiments, the actuator 11 may be electrically powered. For example, the switch 13 for releasing the sprung element 12 referred to above may be electrically powered. Electrical power may also be used to retract the sprung element 12 back to its original non-extended position, thereby also withdrawing the cannula 6. For this purpose, the actuator 11 may comprise an electrical motor 14 and a suitable drive mechanism coupled to the sprung element 12. The electrical power may be provided by a battery 15 or other power source in the device 1, which may be rechargeable.

In particular, the battery 15 may be rechargeable if the configuration of the device 1 is such that the capsule 5 of medicament is replaceable. In this type of configuration, the device 1 comprises a sterile part and a non-sterile part. The sterile part of the device 1 is replaceable and comprises the replaceable capsule 5. The non-sterile part of the device 1 is reusable and comprises reusable elements of the device 1. The elements in the non-sterile part may include, for example, a rechargeable battery 15. In general, the non-sterile part includes elements that do not need to be sterile for safe operation of the device 1 and can be safely reused. It will be appreciated, however, that there is no requirement for the elements that do not need to be sterile to be confined exclusively to the non-sterile part of the device 1. For example, it is possible for the battery 15 to be included with other replaceable elements in the sterile part of the device 1. In this configuration, the battery 15 is non-rechargeable since it is replaced each time the capsule 5 is replaced.

Figure 2:
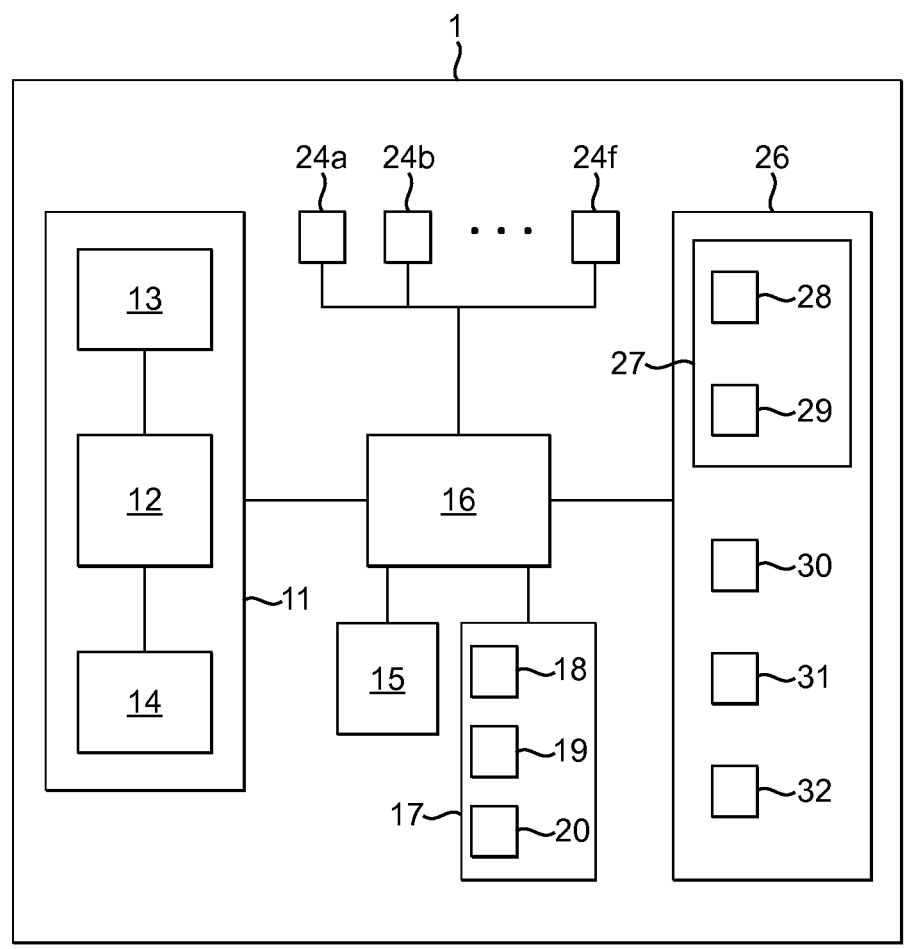
FIG. 2 is a block diagram of the wearable device shown in FIG. 1.

As explained in more detail below, the device 1 comprises an electronic controller 16 which is configured to control operation of one or more elements of the device 1. The electronic controller 16 comprises a processor and a memory and may, for example, comprise an electronic microcontroller which is communicatively coupled to the actuator 11 and/or other elements of the device 1 using a system bus (not shown). The switch 13, motor 14, battery 15 and controller 16 are shown in the block diagram of the device 1 in FIG. 2, but are not shown in FIG. 1.

The device 1 also comprises an alert module 26 which is controlled by the electronic controller 16. The alert module 26 is responsible for outputting alerts to the patient indicating partial detachment of the device 1. As described in more detail hereinafter, alerts can be visual, auditory, or tactile, or alerts can be sent over a wireless network.

The alert module 26 comprises a communications interface so that the device 1 can communicate wirelessly with external devices such as a patient's mobile phone. The communications interface 27 comprises a transceiver 28 and an antenna 29 for transmitting data to and receiving data from the external device.

In the arrangement shown in FIG. 1, data can be transmitted between the device 1 and an external device via a wireless link. The wireless link may be a short range radio communication link. If the wireless communication link uses a protocol such as Bluetooth™, the device 1 and external device will recognise each other when activated and automatically configure the link. If required, the device 1 and external device can be configured to run authentication procedures when configuring the communication link, in order to ensure that the device 1 does not transmit and receive signals from other external devices within its communication range. Alternatively, the link between the device 1 and external device may be provided via a Body Area Network (BAN), in which the body of the patient provides the medium through which the data signals and control signals are transmitted. Other wireless networks could also be used, for example using a cellular or WiFi protocol.

The alert module 26 also comprises an LED 30 for outputting visual alerts to patients indicating partial detachment of the device 1, a buzzer 31 for outputting auditory alerts, and a vibrating alert motor 32 for outputting vibrational alerts. It will be appreciated that these are examples only and that any suitable alternative may be used to provide visual, auditory or vibrational alerts.

The distal end 7 of the cannula 6 may be sharpened to facilitate its insertion into the tissue of the patient. Alternatively, the dispensing interface 4 may also comprise a separate needle (not shown) for aiding the insertion of the distal end 7 of the cannula 6 into the tissue. The needle may be controllably extendable and/or retractable from the housing 2 of the device 1 in a similar manner to the cannula 6 discussed above. The needle is configured to break the skin of the patient in order to allow the cannula 6 to move into the subcutaneous tissue. The needle may, for example, be arranged to extend through the centre of the cannula 6. Once the skin has been broken, the device 1 is configured to retract the needle back into the housing 2 before delivery of the medicament. In the case that the device 1 comprises a separate needle of the type described above, the device 1 may comprise an actuator similar to the one previously discussed in relation to the cannula 6 to facilitate the extension and retraction of the needle.

Another alternative is for the medicament to be delivered through the needle itself. In this case, the needle has properties which are similar to those of conventional injection needles. A proximal end of the needle is connected to the medicament reservoir 3 in a similar manner to the cannula 6 discussed above so that fluid medicament can flow through the needle into the subcutaneous tissue of the patient. If the device 1 is configured in this manner, the cannula 6 may be omitted from the dispensing interface 4.

The flow of medicament into the cannula 6, or other injection element, is controlled by a flow control apparatus 17. As illustrated in FIG. 1, the flow control element may comprise a piston 18 which is moveable through the capsule 5 from one end to the other to drive medicament out of the capsule 5 through the opening 9 referred to above. A suitable drive mechanism (not shown) is mechanically coupled to the piston 18 and is operable to cause the piston 18 to move through the capsule 5. Movement of the piston 18 may be electrically powered. For example, an electric motor 19 may be connected to the drive mechanism. The electric motor 19 is powered by a power source in the device 1, such as the battery 15 referred to previously.

Additionally or alternatively, the flow control apparatus 17 may comprise a seal 20 at the opening 9 in the capsule 5 to prevent medicament from flowing out of the capsule 5 before it is intended that it should do so. The seal 20 is breakable, or openable in some other way, to allow medicament to move from the capsule 5 into the injection element via the conduit 10 referred to previously. The device 1 is configured to operate the flow control apparatus 17, for example by breaking the seal 20 and/or moving the piston 18, in response to a patient-initiated trigger, as explained below.

Figure 3:
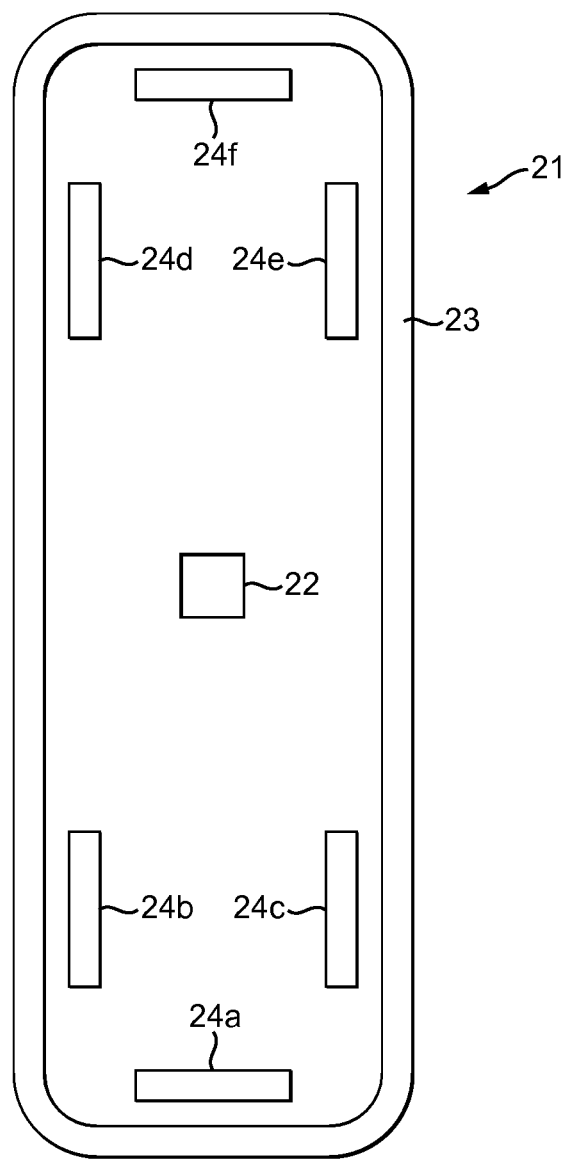
FIG. 3 is a schematic illustration of a patient contact region of the wearable device.

Referring to the exemplary embodiment in FIG. 3, the device also comprises one or more contact sensors 24a-f (also referred to generally herein as contact sensors 24) located proximate the outer edge of the device 1. The sensors 24 are configured to sense contact with the patient's skin at an injection site. These contact sensors are in communication with the electronic controller 16 to provide input signals to the electronic controller 16. The electronic controller 16 can then instruct the alert module 26 to output one or more alerts where appropriate. Moreover, the electronic controller 16 can control the flow mechanism 17 to slow down an injection in response to a partial detachment. The electronic controller 16 can also control the flow mechanism 17 to halt an injection if the degree of detachment of the device 1 from the injection site exceeds an injection halt threshold.

In other words, if the device 1 becomes partially detached but the level of detachment is still below the halt threshold, the flow rate may be slowed. The flow rate may be inversely proportional to the level of detachment of the device so that as the level of detachment increases, the flow rate decreases until the level of detachment reaches the injection halt threshold, at which point the injection is halted.

A contact region 21 of the housing 2 is arranged to be worn against the skin of the patient during use of the device 1. The contact region 21 may, for example, extend at least partially across a generally planar or a generally arcuate surface of the housing 2. The contact region 21 has geometric and tactile properties that are selected to be comfortable when worn against the skin of the patient. It is through the contact region 21 of the housing 2 that the cannula 6, or other injection element, protrudes into the tissue of the patient during delivery of the medicament. The contact region 21 may, for example, comprise an aperture 22 through which the cannula 6 protrudes during use of the device 1. The aperture 22 is large enough to accommodate the cannula 6 and/or the separate needle referred to above, including during the extension and retraction operations previously described.

The contact region 21 comprises the one or more contact sensors 24. The contact sensors can take several forms. The contact sensors may be resistive sensors or capacitive sensors of a type known in the art. Alternatively, the contact sensors may be temperature sensors. When in contact with the patient's skin, a temperature sensor will typically detect a temperature approximating standard human body temperature of around 37 degrees Celsius. However, since the temperature of the skin surface can be less than standard human body temperature, the temperature indicative of skin contact may be less than 37 degrees Celsius. The temperature sensor may be calibrated to take this temperature difference into account. When detached, the measured temperature may drop by an amount indicating loss of contact between the sensor and the patient's skin.

The contact sensors 24 shown in FIG. 3 are positioned around the perimeter of the contact region 21 of the device 1. Positioning the contact sensors around the perimeter enables the device to determine that an edge of the device near to one of the sensors has been detached from the injection site. The layout of the contact sensors 24 can be different in different embodiments. For example, in a circular device the contact sensors may be located around the circumference of the contact region. Additional sensors may also be provided closer to the centre of the device near to the aperture 22.

During use of the device 1, the contact region 21 is held against the skin of the patient by a fastener. The fastener is suitable for holding the contact region 21 in a stable position against the skin for a significant period of time, such as several hours, in order to ensure that the injection element is at all times maintained in a fixed position relative to the body of the patient during use of the device 1. As shown in FIGS. 1 and 3, an example of a suitable fastener is an adhesive layer 23 for temporarily adhering the contact region 21 to the skin of the patient. The adhesive layer 23 may comprise a standard biocompatible glue, as used in common adhesive bandages. In order to protect the adhesive layer 23 from damage and to prevent it from sticking to unwanted objects prior to it being attached to the skin of the patient, the contact region 21 of the device 1 also includes a protective covering (not shown) which overlies the adhesive layer 23. The protective covering is selectively removable from the contact region 21 in order to expose the adhesive layer 23 before use of the device 1, for example by peeling the covering away from the adhesive layer 23.

Figure 4:
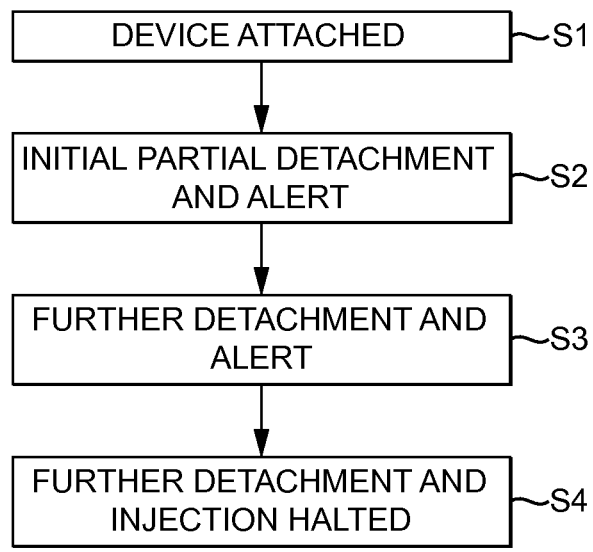
FIG. 4 is a flow diagram of a method of detecting a partial detachment and outputting an alert.

An example will now be described with reference to FIG. 4 to illustrate the functionality of the contact sensors during use of the device 1. At step S1, a patient applies the device 1 to an injection site. The injection site is the location where the medicament is to be injected. Exemplary locations include a patient's upper arms, thighs or abdomen. The device is fastened in place using the adhesive layer 23. The contact sensors 24 detect contact with the patient's skin and output a contact signal to the device controller 16 consistent with attachment of the device 1 to the injection site.

The device 1 is configured to begin delivery of the medicament to the patient in response to a user-initiated trigger. For example, as shown in FIG. 1, the device 1 may comprise a user actuatable element which is located on the exterior of the housing 2 and which the user can operate to cause the device 1 to begin delivery of the medicament. The actuatable element is described below in the context of an electrical switch 34. The switch 34 may be relatively simple to operate in order to improve the usability of the device 1 for the patient. An example is a push-button switch or similar.

At step S2, a region of the contact region 21 near to one of the contact sensor 24*a* becomes detached from the patient's skin. This might be due to the patient accidentally knocking the device 1. The contact sensor 24*a* detects that it is no longer in contact with the skin and a loss of contact signal is output to the device controller 16. In response, the device controller outputs an alert corresponding to the loss of contact of one of the contact sensors 24 with the skin. Since the loss of contact of one sensor is a relatively minor event, a low-level alert is output to the patient. Examples of low level alerts include a light vibrational feedback, actuation of an LED or a low-volume auditory alarm. On detecting the alert, the patient may then re-attach the device 1 to the injection site. Once the device 1 has been re-attached and the contact sensor 24*a* detects contact with the skin, a signal is sent to the device controller and the alert is deactivated.

After the device has been re-attached, a record of the detachment event may be created and stored by the electronic controller 16. The electronic controller 16 may then set a lower detachment threshold for issuing particular alerts or may vary detection parameters for alerting the patient to future detachment of the device 1. For example, while a wireless notification may be issued in response to four of six sensors becoming detached in a first detachment event, in future detachment events, the wireless notification may be issued in response to only three sensors becoming detached.

This is advantageous since, in the event of a partial detachment, there is an increased likelihood of future detachment because of a possible degradation in the adhesive layer that attaches the device to the injection site. In general, it is advantageous to output more severe alerts at an earlier stage in response to future detachment events, thereby reducing the risk of interrupting the injection.

If the patient, for whatever reason, does not re-attach the device at step S2, at step S3 the device 1 may become further detached from the injection site. For example, contact sensor 24*b* becomes detached in addition to contact sensor 24*a* and a loss of contact signal is output to the device controller. In response, the device controller outputs an alert corresponding to the loss of contact of two of the contact sensors 24 with the skin. The alert corresponding to the loss of contact of two of the contact sensors 24 is more noticeable than the previous alert indicating loss of contact with the first contact sensor. For example, an alarm may be sounded at a higher volume than the alarm output when contact with the first sensor was lost. Alternatively, a stronger vibrational alert may be provided.

As well as increasing the volume or strength of the vibrational alert, a different type of alert may be used for different levels of device detachment. For example, a visual alert, e.g. an LED may be output for a single sensor detachment, i.e. a low-level alert, while a vibrational alert may be output when two sensors become detached and an auditory alert may be output when three sensors become detached.

When a relatively high number of contact sensors become detached, for example four of the six sensors shown in FIG. 3, a notification may be sent from the device 1 to an external device, such as the patient's mobile phone. This is especially advantageous since a patient may well carry their phone in their pocket when leaving home. When the patient has left home they can be informed discreetly of the fact that partial detachment of the device has occurred. The notification can take the form of a push notification or an SMS message. The notification to a an external device is particularly advantageous where the patient has no sensation in the area of the body where the injection site is located.

As successively more sensors become detached, the alerts output by the device increase in severity, thereby increasing the chance that the patient will respond and re-attach the device 1 before the device 1 becomes completely detached from the injection site.

As well as analyzing information about the number of detached sensors, information may be obtained regarding the respective positions of detached sensors. In a device having the contact sensor array shown in FIG. 3, if the electronic controller 16 receives respective signals from the sensors 24*a* and 24*b* indicating that those sensors have become detached, the electronic controller becomes aware that the bottom right corner of the device (as shown in FIG. 3) has become detached from the injection site. If the electronic controller 16 receives respective signals from the sensors 24*a* and 24*f* indicating that those sensors have become detached, the electronic controller becomes aware that opposite ends of the device (as shown in FIG. 3) have become detached from the injection site. As such the detachment information can be mapped around the surface of the contact region of the device 1. It will be appreciated that opposite ends of the device becoming detached is more severe than one corner of the device becoming detached. The alert that is output can be made dependent on the detachment information. In the example described above, a more severe alert is output in response to opposite ends of the device becoming detached than if one corner becomes detached.

While successive alerts to indicate partial detachment are output, the injection of the medicament can be continued. As such, the patient's attention can be drawn to the partial detachment of the device 1 and the patient can re-attach the device 1 without an interruption to the injection of the medicament. As described above, the injection flow rate may be reduced as the degree of detachment of the device 1 increases progressively.

If a relatively high number of sensors become detached, the injection of the medicament can be halted at step S4. In the embodiment shown in FIG. 3, there are six contact sensors 24. If, for example, five of the six sensors become detached, the device controller causes the injection mechanism 17 to halt the injection. In the above, the injection device 1 is a patch pump. The injection device may instead be some other form of injection device. The embodiments are particularly suited to bolus injections, but the injection device may instead be of the basal type.

The insertion mechanism for inserting the insertion element may take any suitable form. As described above, it may be a mechanical spring based mechanism. Alternatively, the insertion element mechanism may for instance include an electric motor and a gear mechanism that causes insertion of the insertion element into the user. Alternatively, the insertion mechanism may be a gas or fluid pressure operated mechanism, in which case the needle driving energy source is either a reservoir of pressurised gas or a chemical system in which two or more chemicals are mixed together to produce gas or fluid pressure.

In the foregoing description, resistive, capacitive and temperature sensors have been described. It should be borne in mind that alternative sensors may be used including optical sensors whereby laser light is shone onto the skin and the reflection is detected by a detector and analyzed to determine whether the device is in contact with the skin. Furthermore, capacitive proximity sensors may be used. Proximity sensors can detect objects that are a certain distance away from the sensor. Where proximity sensors are provided, it is not necessary for the sensors themselves to be located on a skin-contacting surface of the device 1.

In an alternative embodiment, a backpressure sensor may be provided in association with the cannula 6 or other injectable element. Such a sensor is configured to detect the backpressure in the cannula during the injection. If the cannula becomes detached, the detected backpressure falls, thereby providing an indication of detachment. A corresponding signal is then sent to the electronic controller 16.

In the above described embodiments, the degree of detachment depends on the number of sensors that become detached. However, in an alternative embodiment one or more sensors can be used, wherein each sensor comprises multiple contact points. Such a sensor outputs a signal to the electronic controller 16 indicating partial detachment of that sensor if some of the contact points become detached.

An individual sensor can also output a continuous range of signals indicative of heavy, light or intermediate contact with the patient's skin. For example, a resistive or a capacitive sensor can output a resistance or capacitance value, respectively, consistent with heavy or light skin contact to the electronic controller 16. If the device 1 becomes partially detached, such values will change and the electronic controller 16 is able to determine that the device 1 has become partially detached and output a suitable alert.

The device 1 is configured to deliver the medicament subcutaneously, although it may instead be configured for intradermal injection, for instance using a microneedle, or for injection in some other manner.

The bolus injector device may be of the type known as a Large Volume Device (LVD). An LVD injection device is configured to dispense a relatively large dose of medicament, in particular at least 1 ml and typically up to 2.5 ml, but possibly up to 10 ml.

The bolus injector device is configured to deliver a bolus of the respective medicament to bring a volume of the medicament into a patient's body within a predetermined time. The injection rate, however, may not be critical, i.e. tight control may not be necessary. However, there may be an upper (physiological) limit to the delivery rate in order to avoid damage to the tissue surrounding the delivery site. The time taken to deliver a bolus dose of medicament may be between a few minutes and many hours depending on a number of factors including the quantity (volume) of medicament, the viscosity of the medicament and the nature of the injection site at which the injection device is intended to be used.

From a user or Health Care Professional perspective, it is desirable for an injection device to be configured to minimally impact the patient's lifestyle and schedule, providing the patient with minimal reminder of his or her disease between the injections. The treatment schedule for therapies is usually intermittent, i.e. may be one injection per week, one injection every other week, or one per month. Therefore, the patient usually has no routine in dealing with his or her disease, and hence has minimal routine/experience in performing the required injections. Thus, configuration of the injection device to simplify its operation by patients is highly desirable.

Because it is intended for bolus operation, the configuration of the injection device is quite different compared to an injection device that is intended to be used for basal operation. Also, its use is quite different. For instance, a basal type insulin pump generally is relatively expensive as it includes many sophisticated diabetes specific features like programmable delivery rate profiles, bolus calculators etc. Further, the connection to the body via an infusion set allows the patient to handle and manipulate the pump in his/her field of view while the therapy is ongoing. Further, diabetes patients usually have a routine in setting-up the infusion set, connecting and operating the pump, and disconnecting the pump temporarily for events like taking a shower so not to expose the pump to water. In contrast, the bolus injector devices described above can be relatively simple and inexpensive devices. They may be provided as single-use devices, which cannot be recharged with medicament, which further reduces complexity and cost.

The term "drug" or "medicament", as used herein, means a pharmaceutical formulation containing at least one pharmaceutically active compound. In some embodiments, the pharmaceutically active compound can have a molecular weight up to 1500 Da or may include a peptide, a protein, a polysaccharide, a vaccine, a DNA molecule, an RNA molecule, an enzyme, an antibody or a fragment thereof, a hormone or an oligonucleotide, or a mixture of the above-mentioned pharmaceutically active compound. Various types or subtypes of compounds are also contemplated. For example, RNA may include RNAi, siRNA, or miRNA. In other embodiments, the pharmaceutically active compound can be useful for the treatment or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis or rheumatoid arthritis. In some embodiments, the pharmaceutically active compound can comprise at least one peptide for the treatment or prophylaxis of diabetes mellitus or complications associated with diabetes mellitus such as diabetic retinopathy. The pharmaceutically active compound can also comprise at least one human insulin or a human insulin analogue or derivative, glucagon-like peptide (GLP-1) or an analogue or derivative thereof, or exendin-3 or exendin-4 or an analogue or derivative of exendin-3 or exendin-4 or a pharmaceutically acceptable salt or solvate thereof.

Insulin analogues can include, for example, Gly(A21), Arg(B31), Arg(B32) human insulin; Lys(B3), Glu(B29) human insulin; Lys(B28), Pro(B29) human insulin; Asp (B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives can include, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 can include, for example, Exendin-4(1-39).

Hormones can include, for example, hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, or Goserelin.

A polysaccharide can include, for example, a glucosaminoglycane, a hyaluronic acid, a heparin, a low molecular weight heparin or an ultra low molecular weight heparin or a derivative thereof, or a sulphated, e.g. a polysulphated form of the above-mentioned polysaccharides, and/or a pharmaceutically acceptable salt thereof. An example of a pharmaceutically acceptable salt of a polysulphated low molecular weight heparin is enoxaparin sodium.

Antibodies can include generally globular plasma proteins (~150 kDa) that are also known as immunoglobulins which share a basic structure. As they can have sugar chains added to amino acid residues, they may also be classified as glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that can include four polypeptide chains; two heavy chains and two light chains connected by disulfide bonds between cysteine residues. Each heavy chain can be about 440 amino acids long; each light chain can be about 220 amino acids long. Heavy and light chains may each contain intra-chain disulfide bonds which stabilize their folding. Each chain is composed of structural domains called Ig domains. These domains typically contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of antibodies can be similar, the unique property of a given antibody is determined by the variable (V) regions, as detailed above. More specifically, variable loops, often three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is usually the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their inter-chain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H inter-chain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion. Pharmaceutically acceptable solvates are for example hydrates.

In some embodiments, medicaments of various viscosities can be injected. For example, viscosity could range from about 3 to about 50 cP. In other embodiments, viscosity could be less than about 3 cP or greater than about 50 cP. Injection can further include delivering a medicament to a sub-cutaneous, an intra-muscular, or a transdermal location within a patient's body. The medicament can be in the form of a liquid, gel, slurry, suspension, particle, powder, or other type.

Typical injection volumes can range from about 1 mL to about 10 mL. Rates of injection may be about 0.5 mL/min, about 0.2 mL/min, or about 0.1 mL/min. Such injection profiles may be generally constant in flow rate, generally continuous in duration, or both generally constant and generally continuous. These injections can also occur in a single step of administration. Such injection profiles may be referred to as bolus injections.

Delivery devices functioning with such medicaments may utilize a needle, cannula, or other injection element configured to deliver a medicament to the patient, as previously discussed. Such an injection element may, for example, have an external size or diameter of 27 G or less. Further, the injection element could be rigid, flexible, and formed using a range of one or more materials. And in some embodiments, the injection element may include two or more components. For example, a rigid trocar may operate in conjunction with a flexible cannula as previously discussed. Initially, both the trocar and cannula may move together to pierce the skin. The trocar may then retract while the cannula remains at least partially within the target tissue. Later, the cannula may separately retract into the delivery device.

The invention claimed is:

1. A medicament delivery device comprising:
   at least one contact sensor configured to output a signal representing a degree of detachment of the medicament delivery device from an injection site, and
   an alert output module configured to receive the signal from the at least one contact sensor and to output an alert when the degree of detachment of the medicament delivery device from the injection site, as represented by the signal, exceeds a detachment threshold indicating a detachment event,
   wherein after the alert is output in response to the detachment event, the medicament delivery device is configured to lower the detachment threshold to be used for indicating a subsequent detachment event.

2. The medicament delivery device of claim 1, wherein the at least one contact sensor is a plurality of contact sensors located at discrete locations on a contact surface of the medicament delivery device.

3. The medicament delivery device of claim 2, wherein some or all of the plurality of contact sensors are disposed proximate to an outer edge of the contact surface.

4. The medicament delivery device of claim 2, wherein the degree of detachment of the medicament delivery device from the injection site, as represented by the signal, exceeds the detachment threshold when a subset of the plurality of contact sensors has become detached from the injection site.

5. The medicament delivery device of claim 1, wherein the medicament delivery device is configured to output one or more further alerts having progressively higher severity levels as the degree of detachment of the medicament delivery device from the injection site, as represented by the signal, increases.

6. The medicament delivery device of claim 1, wherein the medicament delivery device is configured to inject medicament at an injection flow rate, and inject medicament at a reduced injection flow rate when the degree of detachment of the medicament delivery device from the injection site, as represented by the signal, does not exceed an injection halt threshold.

7. The medicament delivery device of claim 1, wherein the medicament delivery device is further configured to halt injection of medicament when the degree of detachment of the medicament delivery device from the injection site, as represented by the signal, exceeds an injection halt threshold.

8. The medicament delivery device of claim 7, wherein the degree of detachment of the medicament delivery device from the injection site, as represented by the signal, is based on (i) a number of the at least one contact sensors that have become detached from the injection site or (ii) a magnitude of the signal output by the at least one contact sensor.

9. The medicament delivery device of claim 1, wherein the medicament delivery device is configured to automatically deactivate the alert when the signal indicates that the medicament delivery device has been re-attached to the injection site.

10. The medicament delivery device of claim 1, wherein the alert is a notification sent through a wireless network to a mobile communications device.

11. The medicament delivery device of claim 1, wherein the alert is at least one of: an auditory alert; a visual alert; or a vibrational feedback alert.

12. The medicament delivery device of claim 1, wherein the at least one contact sensor comprises one or more of a temperature sensor, a resistive sensor, or a capacitive sensor.

13. The medicament delivery device of claim 1, further comprising a controller, wherein the controller is configured to control the alert output module to output the alert based on the signal received from the at least one contact sensor.

14. The medicament delivery device of claim 1, wherein the alert is dependent on information relating to the degree of detachment of the medicament delivery device from the injection site, as represented by the signal.

15. The medicament delivery device of claim 1, further comprising a reservoir of medicament to be delivered into a patient by injection.

16. A method comprising:
   receiving, from at least one contact sensor, a signal representing a degree of detachment of a medicament delivery device from an injection site,
   determining that the degree of detachment of the medicament delivery device from the injection site, as represented by the signal, exceeds a detachment threshold, and
   upon determining that the degree of detachment of the medicament delivery device from the injection site, as represented by the signal, exceeds the detachment threshold, outputting an alert and lowering the detachment threshold to be used for indicating a subsequent detachment event.

17. The method of claim 16, further comprising injecting a medicament.

18. The method of claim 17, further comprising injecting the medicament at an injection flow rate, and injecting medicament at a reduced injection flow rate when the degree of detachment of the medicament delivery device from the injection site, as represented by the signal, does not exceed an injection halt threshold.

19. The method of claim 16, further comprising outputting one or more further alerts having progressively higher severity levels as the degree of detachment of the medicament delivery device from the injection site, as represented by the signal, increases.

20. The method of claim 16, further comprising sending the alert through a wireless network to a mobile communications device.

* * * * *